(12) United States Patent
Brust et al.

(10) Patent No.: US 6,425,296 B1
(45) Date of Patent: Jul. 30, 2002

(54) SUCTION DEVICE

(75) Inventors: Rüdiger Brust, Ziethen; Werner Lurz, Kaltenkirchen; Peter Koch, Norderstedt; Peter Scheffler, Hamburg; Werner Flachsbarth, Norderstedt, all of (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 09/510,051

(22) Filed: Feb. 22, 2000

(30) Foreign Application Priority Data

Feb. 20, 1999 (DE) .......................... 199 07 329

(51) Int. Cl.[7] .............................................. G01N 1/00
(52) U.S. Cl. .................................................. 73/863.23
(58) Field of Search ........................ 73/863.12, 863.23; 422/81; 210/321.6, 321.72, 348, 406, 416.1, 473, 474, 477, 482; 141/65, 181, 250, 275

(56) References Cited

U.S. PATENT DOCUMENTS 3,730,352 A * 5/1973 Cohen et al. ............... 210/406
6,133,045 A * 10/2000 Johnson et al. ............ 210/406

FOREIGN PATENT DOCUMENTS

DE          821616       * 10/1951       ............... 210/406

* cited by examiner

Primary Examiner—Robert Raevis
(74) Attorney, Agent, or Firm—Sidley Austin Brown & Wood, LLP

(57) ABSTRACT

Suction device to draw off sample liquids from filtration vessels to recipient vessels including an evacuable chamber, which has an upper opening with a continues circular sealing surface for marginally supporting at least one filtration vessel mountable in place from top and may be opened for the insertion and removal of at least one recipient vessel, and including a support parallel to the sealing surface to enable the recipient vessel to be positioned in the chamber below the filtration vessel wherein the upper opening including the circular sealing surface is disposed on a first chamber portion adapted to be displaced with regard to a stationarily disposed, second chamber portion including the support where the first and second chamber portions complement each other in a charging position to form a sealed chamber and the first chamber portion releases the support, in an access position displaced away from the second chamber portion, for the insertion and removal of the recipient vessel.

5 Claims, 4 Drawing Sheets

SUCTION DEVICE

The invention relates to a suction device to draw off liquid from filtration vessels to recipient vessels according to the preamble of claim 1.

It is known to separate, add, analyze etc. sample liquids or components thereof by introducing them into filtration vessels and drawing off filtered matter into recipient vessels disposed below them. The filtration vessels have a charging seat with an upper opening to fill in sample liquid, a lower outlet opening for the filtered matter, and a filter associated with it. They may be made of polypropylene, polystyrene or another appropriate material and have a charging capacity of about 10 ml to about 200 µl or less. The filtering materials used are, for example, porous membranes and/or silica and/or diatomaceous earth. Filtration vessels may particularly be individual filtration vessels, arrays of individual filtration vessels, strip-type filtration vessels, arrays of strip-type filtration vessels or microtitration filter plates (also referred to as "membrane-type microtitration plates"), the latter comprising a multiplicity of recipent vessels in a matrix arrangement which corresponds to the matrix arrangement of a membrane-type microtitration plate.

To draw the sample liquid off, at least one filtration vessel is mounted in a marginally sealing way on a suction device so that its outlet opening faces an evacuable chamber of the suction device. At least one recipient vessel is disposed in the chamber below the at least one filtration vessel, which receives the sample liquid trickling down from the filtration vessel. An individual filtration vessel, an array of individual filtration vessels, a strip-type filtration vessel or an array of strip-type filtration vessels may be disposed in a perforated plate or another mounting and may be disposed across them in a marginally sealing way on a suction device. Accordingly, the various designs of the recipient vessels may be disposed in a mounting.

A suction device of the type mentioned at the beginning including an evacuable chamber which has an upper opening with a continuous circular sealing surface which approximately extends horizontally for marginally supporting a membrane-type microtitration plate mountable in place from top and may be opened for the insertion and removal of a microtitration plate recipient vessel, and including a support to enable the microtitration plate recipient vessel to be positioned in the chamber below the membrane-type microtitration plate and in parallel thereto is known from DE 41 07 262 C2. To improve the handling properties and to reduce the hazard of contamination, the support of the microtitration plate recipient vessel is disposed on a carrier which is adapted to be displaced, through a feed opening of the chamber, up to a charging position in the chamber, in which the microtitration plate recipient vessel will then be disposed below the membrane-type microtitration plate, the carrier is connected to a front plate which sealingly bears on the edge of the feed opening in a charging position, and the carrier is adapted to be displaced from the chamber, through the feed opening, into an access position for the insertion and removal of the microtitration plate recipient vessel.

In this suction device, the membrane-type microtitration plate and the microtitration plate recipient vessel are positioned and removed manually. While the microtitration plate recipient vessel is being displaced by means of the drawer-like carrier accelerations and concussions may occur by which sample liquid may drop down from the membrane-type microtitration plate or flow over from recipient vessels. This can lead to liquid losses and contaminations of the recipient vessels and the chamber. Already for this mere reason, an automation of the charging and discharging operations for the suction device would pose a problem.

The filtration vessels and recipient vessels require to be aligned to each other as precisely as possible in the suction device. Errors of alignment, pull-off effects, and aerosol formation may also cause losses and contaminations during the transfer of filtered matter from filtration vessels to recipient vessels. Also, for an optimum transfer of filtered matter, filtration vessels of a special drop-down contour which are centrally aligned to the matching recipient vessel have already been proposed.

DE 41 27 276 C2 discloses a sample liquid separation device wherein a filtration vessel has moulded to it an outlet tube joining an outlet opening and a socket surrounding the tube, on which a recipient vessel is adapted to be attached such that an exchange of air is possible between the interior of the recipient vessel and its surroundings. The outlet tube protrudes beyond the socket into the recipient vessel so that a drop which is at the end of the outlet tube does not get into the area of contact of the filtration vessel and recipient vessel. It is true that a loss of liquid and contamination are largely avoided by the device. However, the arrangement of the filtration vessel and recipient vessel with regard to each other and to a suction chamber is an expenditure and is carried out manually.

Accordingly, it is an object of the invention to create a suction device which favours low-loss and low-contamination operation and automation thereof.

The object is attained by a suction device having the features of claim 1, further by a suction device having the features and, finally, by a suction device having the features. Advantageous aspects of the suction devices are indicated in the sub-claims.

The first solution variant is characterized in that the upper opening having the continuous circular sealing surface is disposed on a first chamber portion which is adapted to be displaced with regard to a stationarily disposed, second chamber portion having a support, the first and second chamber portions complementing each other to form a sealed chamber in a charging position and the first chamber portion releases the support for the insertion and removal of the at least one recipient vessel in an access position displaced away from the second chamber portion. The first chamber portion may be adapted to be displaced here, particularly in parallel with or perpendicularly to the support.

The fact that the second chamber portion having the support is disposed stationarily prevents a recipient vessel positioned on the support from being moved while the first chamber portion is being displaced, which avoids liquid losses and contaminations. For the same reason, it is possible to position the filtration vessel on the first chamber portion only after the latter is displaced into the charging position and to remove the vessel from the first chamber portion before the latter is displaced into the access position. In addition, auxiliary means associated with the stationary support may be realized at a lower expenditure. Altogether, this will also favour the automation of suction device operation.

The second solution variant is characterized in that the chamber has at least one lateral opening including a closure, which releases the opening into an access position for the insertion and/or removal of at least one recipient vessel and sealingly closes the opening in a charging position, and that the recipient vessel is adapted to be displaced from an access position disposed outside the chamber, through the opening, into a charging position below the position of the filtration vessel, and vice versa. The displacement of the recipient vessel may preferably be effected along a guide.

Since the recipient vessels are of a relatively small weight accelerations and concussions which can lead to mixing and the loss of liquid may be avoided during the insertion and removal of the recipient vessels, which may be performed without any concurrent displacement of further device components. Moreover, the mere displacement of the recipient vessels will favour the rapid succession of suction operations and the easy design of auxiliary means. Altogether, this will favour automation as well.

The third solution variant is characterized in that the support is adapted to be vertically displaced towards the upper opening by means of a lifting device within the chamber to dispose the recipient vessel close to the filtration vessel in a charging position.

The approach of the recipient vessel to the filtration vessel, which can be effected until the recipient vessel is moved in part onto the filtration vessel, serves to avoid losses and contaminations when the filtered matter flows out. By means of the lifting device, a displacement within the closed chamber may be caused, which helps avoid an expenditure in manual positioning. The lifting device is an auxiliary means acting on the recipient vessel so that the third solution variant can be realized in a particularly advantageous way along with the first solution variant or the second solution variant. Even this solution variant will favour an automation of suction device operation.

The invention will now be explained in detail with reference to the accompanying drawings of some embodiments, in which.

Components which are coincident are designated by identical reference figures in the following description of various embodiments. In this respect, the description will apply to all embodiments concerned. It is true that all embodiments relate to the use of membrane-type microtitration plates and microtitration plate recipient vessels. However, they are generally suited for use also with other filtration vessels and recipient vessels of the type mentioned at the beginning, possibly in connection with appropriate mountings.

Figure 1:
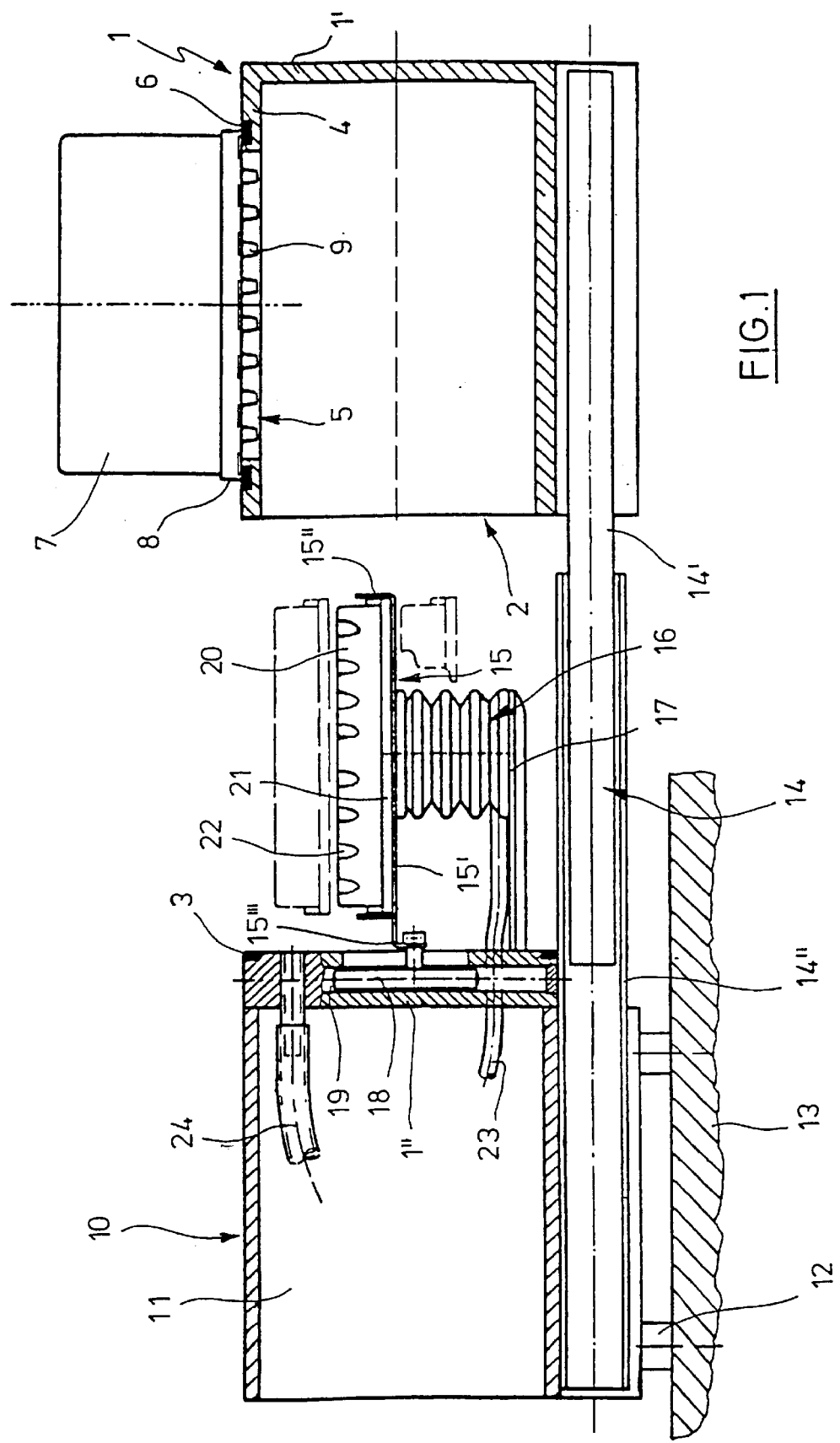
FIG. 1 is a vertical cross-section of a suction device having a horizontally displaceable first chamber portion and a support with a pneumatic lifting device in an access position.

The suction device of FIG. 1 has a box-shaped chamber 1 comprised of a first chamber portion 1' and a second chamber portion 1". Here, the second chamber portion 1" merely defines a vertical, lateral wall of chamber 1 the remaining part of which is defined by the first chamber portion 1'. A lateral opening 2 of the first chamber portion 1' is defined by the second chamber portion only when the device is in its charging position and is opened in an access position which is shown. The second chamber portion 1" has disposed in a marginally continues circular groove a sealing material 3 (e.g. a sealing string), which sealingly bears on the edge of the lateral opening 2 of the first chamber portion 1' in a charging position.

The first chamber portion 1' has an upper opening 5 in a horizontal upper wall 4. A groove into which a sealing material 6 (e.g. a sealing string) defining an approximately horizontal sealing surface at top is inserted, extends in the upper wall 4 in a position close to the edge of the upper opening 5.

A membrane-type microtitation plate 7 is placed on top of the first chamber portion 1' in such a way that its edge 8 sealingly rests on the sealing material 6. The membrane-type microtitation plate has charging seats (not shown) which can be tilled with liquid through top openings. At bottom, said charging seats are connected to outlet openings defined at the ends of drop-down contours 9 in the form of small cones. Filtering agents are in the charging seats, drop-down contours or outlet openings. Membrane-type microtitration plates 7 of this type have been known. Common designs are equipped with 96 or 384 charging seats.

The upper openings of the charging face the surroundings and the outlet openings face the interior of chamber 1.

Moreover, the second chamber portion 1" permanently defines a vertical lateral wall of a stationary shell 10 having a chamber 11, especially for accommodating auxiliary means which, for instance, might form part of a drive, a vacuum controller, a sensor mechanism or a control unit. Shell 10 has firm connections 12 to an automatic sample preparing unit 13 of which more details are not shown here. However, such connection to an automatic sample preparing unit is only one advantageous application of the suction device. Merely the stationary arrangement of the second chamber portion 1" is essential.

The first chamber portion 1' and the second chamber portion 1" are connected to each other by a horizontally aligned sliding guide 14. This has at least one first slide rail 14' which is firmly connected to the underside of the first chamber portion 1' and at least one second slide rail 14" which is firmly connected to the underside of the second chamber portion 1' and the shell 10. The first slide rail 14' is adapted to be horizontally displaced along the second slide rail 14". This makes it possible to move the first chamber portion 1' connected to the first slide rail 14', in a pure horizontal motion, from the access position shown to the charging position in which the edge of its lateral opening 2 sealingly rests on the edge of the second chamber portion 1".

Disposed on the side of the second chamber portion 1" facing the first chamber portion 1' is a support 15, which has a charging seat defined by a horizontal carrier plate 15' and upright side walls 15" extending from it. The bottom of carrier plate 15' rests on a pneumatic lifting device 16. The lifting device 16, in turn, is sustained at bottom on a carrier 17 which horizontally projects from the second chamber portion 1" and is fixed thereto.

The carrier plate 15' passes over, on the side of the second chamber portion 1", to form the horizontal leg of an angular portion 15''' the vertical leg of which is laterally fixed to a guide bar 18 which is adapted to be displaced in a vertical bore 19 of the second chamber portion 1". This enables support 15 to be guided in a vertical direction. The upper and lower ends of bore 19 define stops for guide bar 18 which limit the vertical motion of support 15 onto the area of the double arrow marked by the word "lift".

Placed on the support 15 is a microtitration plate recipient vessel 20. It is sustained, at bottom, on the carrier plate 15' by a lower edge 21 and, laterally, on the side walls 15". The microtitration plate recipient vessel 20 comprises recipient vessels 22 which are open at top and the number and arrangement of which corresponds to that of the membrane-type microtitration plate recipient vessel 7.

Connected to the pneumatic lifting device 16 is a line 23 which is passed into chamber 11 through a sealing bushing of the second chamber portion 1". The way of operation of line 23 will be referred to below.

In addition, a vacuum line 24 is sealingly passed through the second chamber portion 1" so as to open into the interior of chamber 1. A vacuum pump (not shown) which is arranged in chamber 11, may be connected, for example, to the other end of vacuum line 24.

The pneumatic lifting device 16 may comprise a pneumatic cylinder having a suitable attenuating member. The pneumatic cylinder is supported, at bottom, on carrier 17 and its actuator is connected to the carrier plate 15' at top.

The activating mechanism (not shown) of the pneumatic lifting device 16 comprises an electrically operable three-way valve and an air supply. The pressure-end connection of the vacuum pump for discharging chamber 1 may be used for this purpose.

When chamber 1 is opened a microtitration plate recipient vessel 20 is inserted in the charging seat of support 15 with the pneumatic lifting device 16 being in the lowermost position. After chamber 1 is closed the three-way valve releases the lift connection of the pneumatic lifting device 16 such that the compressed air provided by the air supply elevates support 15 with the microtitration plate recipient vessel 20.

The lifting motion will be interrupted by the upper stop when it is reached or by a sensor integrated in the second chamber portion 1" (e.g. a reflection-type light barrier or a Hall effect component) when the microtitration plate recipient vessel 20 was lifted to a defined position with regard to the drop-down contours 9 of the membrane-type microtitration plate 7 disposed or yet to be disposed on the upper opening 5 of suction chamber 1. It is at this point at the latest that the membrane-type microtitration plate 7 is placed onto sealing 6.

Only after the pneumatic lifting device 16 and the membrane-type microtitration plate 7 are positioned suction chamber 1 is evacuated and filtrated matter is collected in the microtitration plate recipient vessel 20. This especially prevents cross-contamination of adjoining recipient vessels 22.

Upon completion of the suction process chamber 1 is ventilated to achieve ambient pressure again. The three-way valve, when changed over, reverses the pneumatic drive, the elevating device 16 slowly moves downwards (e.g. for about 2 seconds) until the the lower stop is reached. Chamber 1 may then be opened by displacing the first chamber portion 1" for the removal of microtitation plate recipient vessel 20.

Instead, the pneumatic elevating device 16 may be designed as corrugated bellows with an appropriate attenuating member. The bellows 16 may be connected to the ambient air via line 23 and a non-return valve (not shown). Once an interlocking device of the first chamber portion 1" is closed on the second chamber portion 1 and the vacuum pump is started the pressure in chamber 1 will slowly lower below atmospheric pressure. The bellows 16 connected to the ambient air via line 23 will blow up and lift support 15 with the microtitration plate recipient vessel 20 towards the microtitration filter plate 7 until an upper stop is reached. The bellows 16 has been designed so as to ensure the lifting action across the entire vacuum working range of chamber 1.

If the vacuum should collapse in chamber 1 because of defect-related untightnesses such as a rupture of one of the filtration membranes of the filtration vessel array or because of defective sealings the microtitration plate recipient vessel 20 is maintained in the elevated position. The reason is that the integrated non-return valve will prevent the bellows 16 from collapsing when there is no vacuum in chamber 1.

Not until the interlocking is released between chamber portions 1', 1" the non-return valve will be opened. The bellows 16 is aerated and lowers the support 15 with the microtitration plate recipient vessel 20.

Figure 2:
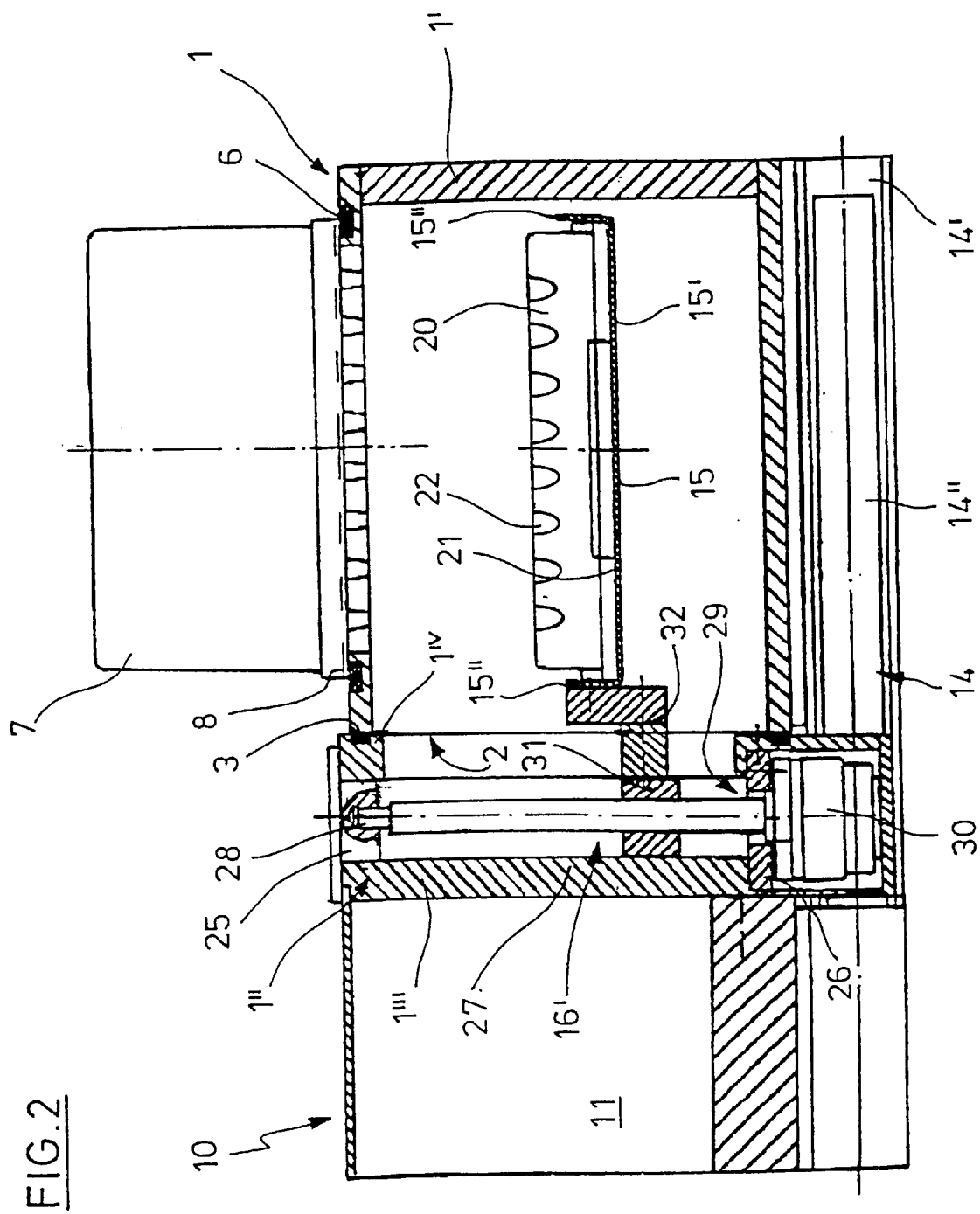
FIG. 2 is a vertical cross-section of a suction device having a horizontally displaceable first chamber portion and a support with an electric lifting device in a charging position.

The suction device of FIG. 2 has an electric-motor driven lifting device 16', which is integrated in the second chamber portion 1". To this end, the vertical wall of the second chamber portion 1" has two parallel wall sections 1''', $1^{IV}$, which are kept at a spacing from each other by means of two plates 25, 26 both at top and bottom.

A spindle 27 is disposed between wall sections 1''', $1^{IV}$, which is supported at top on a journal 28 in plate 25 and extends at bottom through a central bore 29 of plate 26. Spindle 27 is connected at bottom in an anti-rotation way to the driving shaft of the electric-motor drive 30 (e.g. a stepping motor) which is firmly connected to the second chamber portion 1", e.g. by flanging its front-end face to the plate 26.

Seated on the spindle 27 by a female thread is a slider 31 which is guided outside on inner surfaces of the second chamber portion 1" such that it may be vertically displaced by rotating the spindle 27. A support 15 is connected to the slider 31 via an angled part 32.

An activation unit (not shown) of the electric-motor drive is comprised of an electronic switching unit with a controller and a rotation reversal device.

Sealing string 3 is accommodated in a marginally continuous circular groove of wall section $1^{IV}$ of the second chamber portion 1". The first chamber portion 1' is configured as in the embodiment of FIG. 1. Likewise, the horizontal slide rail 14 between the first chamber portion 1' and the second chamber portion 1" largely coincides with that of FIG. 1.

When chamber 1 is opened a microtitration plate recipient vessel 20 is inserted in the charging seat of support 15. At this point, lifting device 16' will be in its lowermost position. When the chamber 1 is closed the controller sets the electric-motor drive 30 to work. The spindle 27 which rotates elevates support 15 with the microtitration plate recipient vessel 20.

An upper stop or an sensor integrated in the second chamber portion 1" (e.g. a reflection-type light barrier, a Hall effect element) interrupts the lifting motion when the microtitration plate recipient vessel 20 has been elevated to a defined position with respect to the drop-down contours 9 of the microtitration filter plate 7 placed on the upper opening 5 of chamber 1.

Not until then, chamber 1 is evacuated and filtered matter is collected in the microtitration plate recipient vessel 20. This especially avoids cross-contamination of adjoining reception vessels 22.

Upon completion of the suction process, chamber 1 is aerated to ambient pressure again. The sense of rotation of the electric-motor drive 30 is reversed. Then, support 15 will slowly move downwards (e.g. for about 2 seconds) until another defined position is reached. After this, chamber 1 may be opened for removal of the microtitration plate recipient vessel 20 by a horizontal displacement of the first chamber portion 1".

In the case of the suction chambers of FIGS. 1 and 2, the first chamber portion 1" may be displaced by hand or by means of an appropriate drive (e.g. pneumatic, electric-motor). In lieu of the linear displacement shown, a displacement—both by hand or by means of an appropriate drive—may be effected by pivoting wherein the first chamber portion 1" may be pivotally supported on the second chamber portion 1".

What applies to all of the aforementioned suction devices is that the microtitration plate recipient vessel 20 is exclusively subjected therein to vertical motions, which also avoids losses and contaminations. This is even favoured when the membrane-type microtitration plate 7 is not put in place or removed in an access position, but in a charging position. These devices are suited particularly for the automated mode of operation, also because of the auxiliary means associated with the second chamber portion 1".

Figure 3:
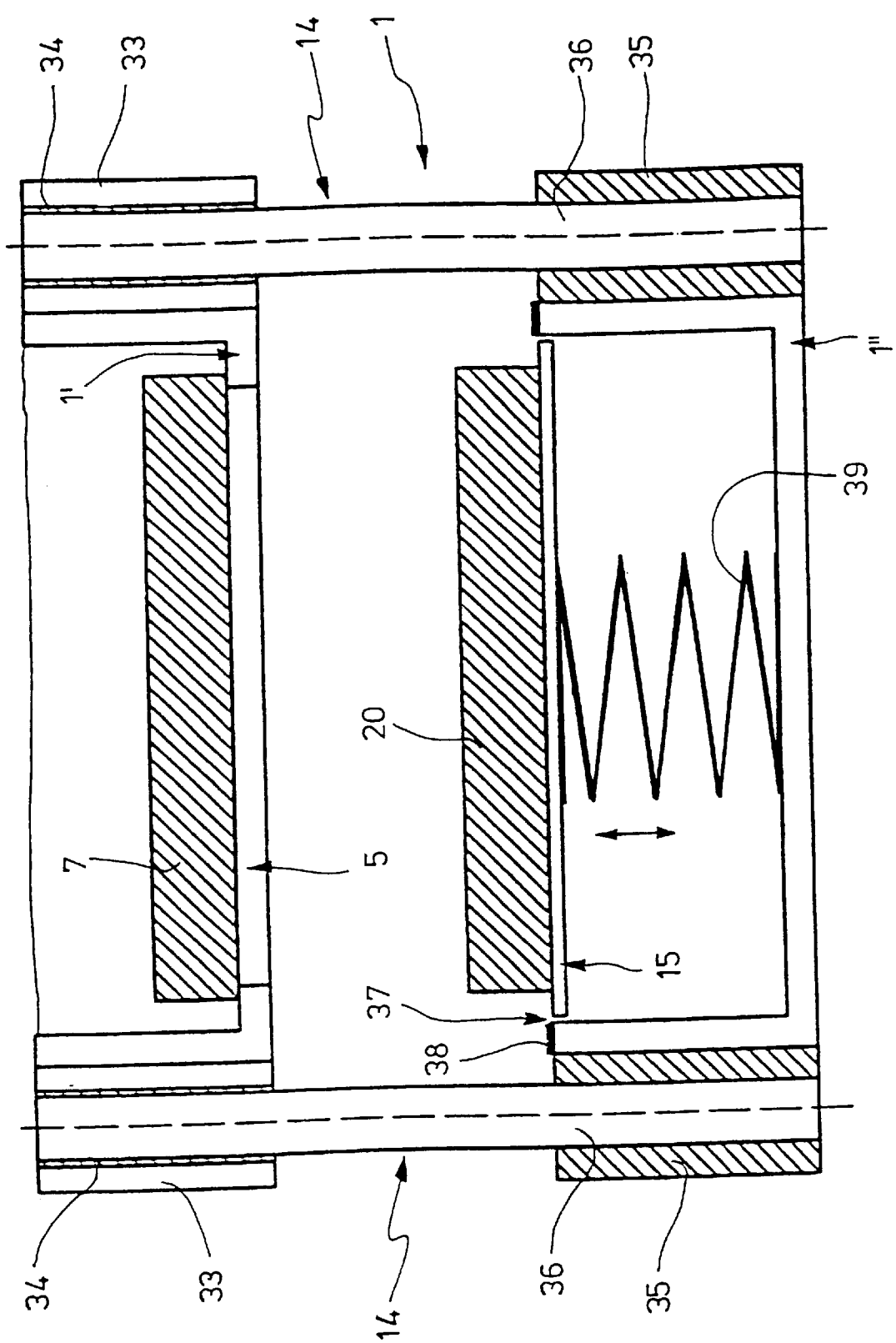
FIG. 3 is a vertical cross-section of a suction device having a vertically displaceable first chamber portion and a support with a resilient lifting device in an access position.

According to FIG. 3, one chamber 1 is of a rectangular configuration as well. A first chamber portion 1' is designed as an upper chamber wall to close a tray-like second chamber portion 1". Here, the first chamber portion 1' comprises the upper opening 5 and has lateral holders 33 moulded in place with slide bushes 34 which are inserted.

The second chamber portion 1" also has lateral holders 35 moulded in place in which bars 36 are fixed on which sliding bushes 34 are disposed to define two vertical sliding guides 14. Hence, the first chamber portion 1' is adapted to be vertically displaced along the bars 36 with regard to the second chamber portion 1".

A sealing material 38 extends around the edge of an upper opening 37 of the second chamber portion 1". When the upper chamber portion 1' has reached its lowermost position it will sealingly be supported by the lateral edge of its opening 5 on the upper, horizontal sealing surface of sealing material 38.

The upper edge of opening 5 of the first chamber portion 1' marginally supports a membrane-type microtitration plate 7 put in place from top.

A horizontal support 15 is disposed in the lower chamber portion 1". The support is sustained at the bottom of the second chamber portion 1" via a resilient means 39 (e.g. a compression spring). The resilient means 39 is dimensioned so as to dispose the support 15 approximately at the level of the upper opening 37 of the second chamber portion 1 with the microtitration plate recipient vessel 20 placed on top as is shown in FIG. 3.

In the access position shown, a microtitration plate recipient vessel 20 is first placed on support 15. The microtitration filter plate 7 may be placed on top in this position. To avoid concussions, however, this may also be done at a later point. After this, the first chamber portion 1' is displaced downwards wherein the lower edge of opening 5 bears against the upper edge of microtitration plate recipient vessel 20, displacing it downwards against the action of the resilient means 39 until the lower edge of opening 5 comes to rest on sealing material 38. In this closed arrangement of chamber 1, the microtitration plate recipient vessel 20 is elastically urged by the resilient means 39 against the lower edge of opening 5. Hence, the resilient means provides, with microtitration plate recipient vessels 20 of different height, for the upper sides thereof to be arranged always at the same level such that a spacing which is always the same is maintained from the exit openings of a membrane-type microtitration plate.

It is at this point at the latest that the membrane-type microtitration plate 7 is placed onto the upper edge of opening 5, preferably onto a sealing material (not shown). With chamber 1 in a closed arrangement the membrane-type microtitration plate 7 may engage charging seats of microtitration plate recipient vessels 20 by means of drop-down contours (not shown).

Subsequently, the chamber is evacuated to draw off the filtered matter lying on the microtitration filter plate 7 into the microtitration plate recipient vessel 20.

Upon completion of the suction process, microtitration filter plate 7 may first be removed, and the upper chamber portion 1 may then be moved up until an upper stop is reached. After this, microtitration plate recipient vessel 20 is removed.

Losses and contaminations are avoided, particularly because of the exclusively vertical motion of the microtitration plate recipient vessel only by short distances.

Figure 4:
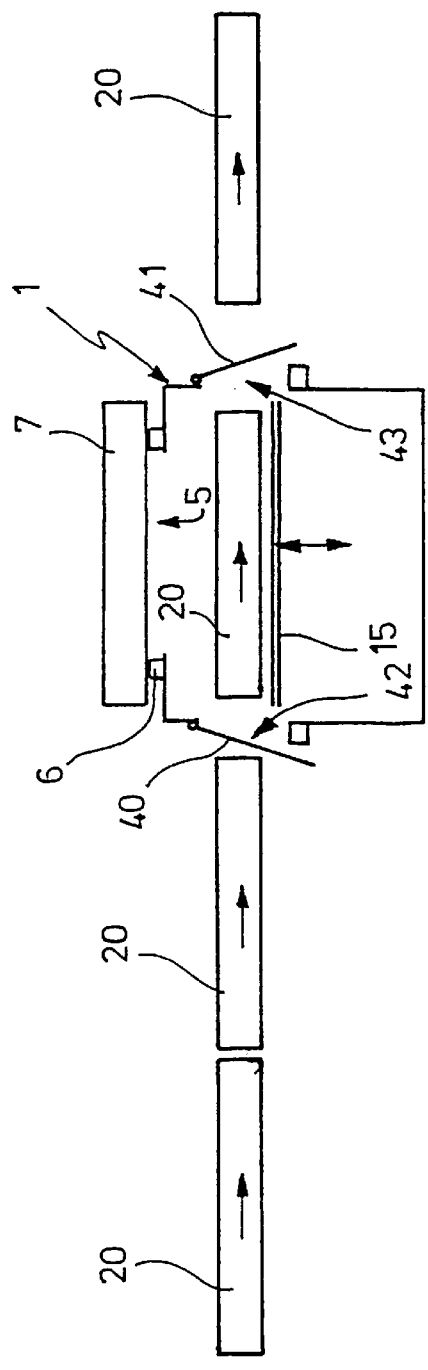
FIG. 4 is a roughly schematic vertical cross-section of a suction device having a lateral opening for the insertion and another lateral opening for the removal of microtitration panel recipient vessels in a charging position.

According to FIG. 4 there is an evacuable chamber 1 which is substantially rectangular and, in turn, has an upper opening 5 around the edge of which a sealing material 6 extends circularly to support a membrane-type microtitration plate 7.

Chamber 1 has disposed on two opposed sidewalls closures in the form of flaps 40, 41 which are pivotable about a horizontal axis from a closed position, while contacting chamber 1, to an opened position. When in a closed position, flaps 40, 41 sealingly bear against edges of associated openings 42, 43 of the side walls.

Chamber 1 houses a horizontal support 50 which is vertically movable upwards and downwards by means of a lifting device (not shown) in the direction of the arrow "lift". A microtitration plate recipient vessel 20 rests on the upper surface of support 15.

The microtitration plate recipient vessel 20 is aligned at the level of openings 42, 43 in the lowermost position shown for support 15. The microtitration plate recipient vessel 20 may be displaced towards the membrane-type microtitration plate 7 by actuating the lifting device until an upper stop is reached. The upper stop may be defined by the lower edge of the upper opening 5.

In addition, guides parallel to the image plane may exist, along which a microtitration plate recipient vessel 20 is adapted to be displaced from outside to the support 15 through opening 42 and, thence, to the outside through opening 43.

As is shown in the figure microtitration plate recipient vessels 20 may be lined up in front of chamber 1 and may successively be resorted to for suction processes by pushing them into opening 42 and pushing them out of opening 43. The two flaps 40, 41 are opened before the recipient vessels are pushed in and out. At this point, a microtitration plate recipient vessel 20 placed on support 15 may be forced forward by a succeeding microtitration plate recipient vessel 20 so that only one drive need exist on the side of opening 42.

Moreover, the membrane-type microtitration plate 7 may be changed every time a microtitration plate recipient vessel 20 is changed. To avoid losses and contaminations a membrane-type microtitration plate 7 already subjected to the suction process may be removed before microtitration plate recipient vessel 20 is removed from support 15 and a new membrane-type microtitration plate 7 may be placed upon the upper opening when an empty microtitration plate recipient vessel 20 has been placed already on support 15.

Figure 5:
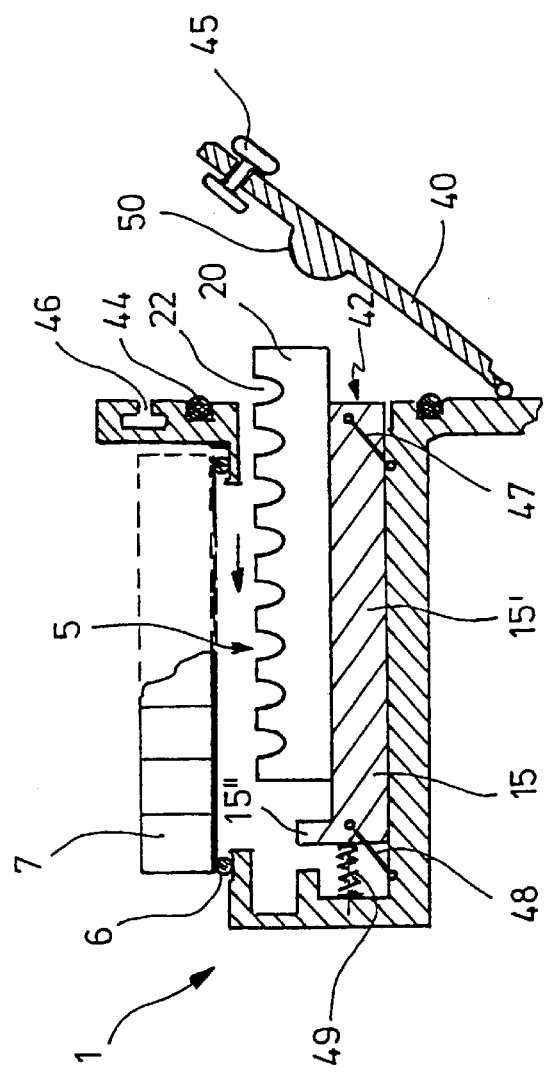
FIG. 5 is a vertical cross-section of a suction device having a having a lateral opening for the insertion and another lateral opening for the removal of microtitration plate recipient vessels, and a parallelogram linkage for the displacement of the microtitration plate recipient vessel to the membrane-type microtitration plate in an access position.

The suction device of FIG. 5, in turn, has an evacuable chamber 1 which is substantially rectangular and has an upper opening 5 the edge of which is surrounded by a sealing material 6. A membrane-type microtitration plate 7 may be sealingly placed on it.

Further, associated with one side of chamber 1 is a flap 40 which serves to close a lateral opening 42 of chamber 1. To this effect, flap 40 is horizontally hinged at bottom and may be pressed against a sealing material 44 surrounding the opening 42 to seal chamber 1 laterally. For an interlocking effect, flap 40 has an locking means 45 at top and chamber 1 has a complementary locking means 46 at its side.

Above the bottom of chamber 1, there is a support 15. It has a carrier plate 15' including a side wall 15", which stands upright at the inner end of carrier plate 15'.

Support 15 is sustained at the bottom of chamber 1 via a parallelogram linkage which is defined by at least two parallel articulated bars 47, 48 which are jointed on support 15 at one end and on chamber 1 at the other. Besides, the inner end of support 15 is sustained on a side wall of chamber 1 opposite to lateral opening 42 via a compression spring 49.

As is shown in FIG. 5 when a suction process is intended to be effected a microtitration plate recipient vessel 20 is pushed in through opening 42 from the side until side wall 15" is reached, as a maximum. Flap 40 is then pivoted so as to close while a convexity 50 disposed at its inside bears against the outer end of microtitration plate recipient vessel 20. As a result, microtitration plate recipient vessel 20 continues to be pushed in, carrying along support 15 via side wall 15". At this point, parallelogram linkage 47, 48 causes support 15 to lift and, thus, microtitration plate recipient vessel 20 to be moved to the upper opening 5. At the same time, spring 49 undergoes pretensioning. Once flap 40 is closed it will be locked on chamber 1 with the aid of means 45, 46.

After this point at the latest, membrane microtitration plate 7 is placed with drop-down contours 9 being adapted to extend into upper openings of seats 22. The suction device will then be in the charging position and evacuation of chamber 1 may start.

Upon completion of the suction process, membrane-type microtitration plate 7 is preferably removed first. Then, flap 40 is opened and microtitration plate recipient vessel 20 is moved back, by the action of spring 49, to an access position which can be readily got at from outside.

These charging and discharging processes are also of the low-loss and low-contamination type and are susceptible of automation at a comparatively low expenditure.

The insertion and removal of the microtitration plate recipient vessel and membrane-type microtitration plate may be effected both manually and auto-matically in all of the cases and an automatic device may have a gripper to take hold of the microtitration plate recipient vessel or the membrane-type microtitration plate.

What is claimed is:

1. A suction device for drawing off a sample liquid from filtration vessels (7) to recipient vessels (20), the suction device comprising an evacuable chamber (1) having an upper opening (5) with a continuous circular sealing surface (6) for supporting at least one top-mountable filtration vessel (7) at a filtration vessel edge and openable for insertion and removal of at least one recipient vessel (20); and a support (15) arranged parallel to the sealing surface (6) and beneath the sealing surface (6) for receiving the at least one recipient vessel (20) for positioning the at least one recipient vessel (20) below the filtration vessel (7), wherein the evacuable chamber (1) is formed of a stationary, second chamber portion (1") and a first chamber portion (1') displaceable relative to the stationary, second chamber portion (1"), the first and second chamber portions (1' and 1") complementing each other to form a sealed chamber in a charging position of the suction device, wherein the upper opening (5), together with the sealing surface (6), is located in the first chamber portion (1') that releases the support (15) in an access position of the first chamber portion (1'), in which the first chamber portion (1') is displaced from the second chamber portion (1"), providing for insertion and removal of the least one recipient vessel (20), and wherein the suction device further comprises a sliding guide (14) for enabling displacement of the first chamber portion (1") relative to the second chamber portion (1").

2. The suction device according to claim 1, wherein the sliding guide comprises bush means, and bars (36) which are guided in the bush means.

3. The suction device according to claim 1, comprising means for displacing the support (15) perpendicular relative to the first chamber portion (1').

4. The suction device according to claim 3, wherein the second chamber portion (1") has an upper opening (37), and the first chamber portion (1') is formed as an upper chamber wall that closes the upper opening (37) of the second chamber portion (1") in the charging position.

5. The suction device according to claim 1, wherein the first chamber portion (1') and the second chamber portion (1") have a horizontal separation plane.

* * * * *